(12) United States Patent
Kang et al.

(10) Patent No.: US 9,168,212 B2
(45) Date of Patent: Oct. 27, 2015

(54) COMPOSITION FOR EYELASH GROWTH

(75) Inventors: Sang-hwan Kang, Gyeonggi-do (KR); Keun-Ho Ryu, Seoul (KR); DongChul Shin, Gyeonggi-do (KR); Bong-yong Lee, Seoul (KR)

(73) Assignee: SK CHEMICALS CO., LTD., Gyeonggi-Do (KR)

( * ) Notice: Subject to any disclaimer, the term of this patent is extended or adjusted under 35 U.S.C. 154(b) by 203 days.

(21) Appl. No.: 14/124,821

(22) PCT Filed: Jun. 8, 2012

(86) PCT No.: PCT/KR2012/004540
§ 371 (c)(1),
(2), (4) Date: Feb. 5, 2014

(87) PCT Pub. No.: WO2012/169827
PCT Pub. Date: Dec. 13, 2012

(65) Prior Publication Data
US 2014/0194501 A1      Jul. 10, 2014

(30) Foreign Application Priority Data

Jun. 8, 2011 (KR) .................... 10-2011-0055233

(51) Int. Cl.
| | | |
|---|---|---|
| A61K 8/49 | (2006.01) | |
| A61K 31/352 | (2006.01) | |
| A61Q 7/00 | (2006.01) | |
| A61K 31/5575 | (2006.01) | |
| A61K 31/5578 | (2006.01) | |

(52) U.S. Cl.
CPC .............. *A61K 8/498* (2013.01); *A61K 31/352* (2013.01); *A61K 31/5575* (2013.01); *A61K 31/5578* (2013.01); *A61Q 7/00* (2013.01)

(58) Field of Classification Search
None
See application file for complete search history.

(56) References Cited

U.S. PATENT DOCUMENTS

| 6,262,105 B1 | 7/2001 | Johnstone et al. ...... A61K 31/38 |
| 7,816,399 B2 * | 10/2010 | Orihashi et al. .............. 514/456 |

FOREIGN PATENT DOCUMENTS

KR      10-2006-0120424      11/2006      ........... A61K 31/496

OTHER PUBLICATIONS

Melamed, S, et al.; "*Effectiveness of Bimatoprost (LUMIGAN) as Adjunctive Theraphy with Topical Beta-blockers in Patients with Glaucoma or Ocular Hypertension: A 3-Month, Multi-center, Double-masked, Randomized, Vehicle-controlled Trial with Double-masked Extension of Bimatoprost Treatment to 1 Year.*" Annual Meeting of the Association for Research in Vision and Ophthalmology: Fort Lauderdale, Florida, USA; May 5-10, 2002. Abstract Only.

Yoshitomi, Takeshi, et al.; "*Vasodilatory effects of nipradilol, an alpha-and beta-adrenergic blocker with nitric oxide releasing action, in rabbit ciliary artery.*", Experimental Eye Research, vol. 75, No. 6, Dec. 2002, pp. 669-676.

Tsuru, T. et al. "*The additive effects on intraocular pressure of combining nipradilol 0.25% and latanoprost 0.005% ophthalmic solutions: A prospective, randomized, multicenter study*", Japanese Journal of Ophthalmology 200809JP, vol. 52, No. 5, Sep. 2008, pp. 368-373.

International Search Report (ISR) with English Translation and Written Opinion (WO), dated Dec. 5, 2012 in PCT/KR2012/004540.

\* cited by examiner

*Primary Examiner* — Bong-Sook Baek
(74) *Attorney, Agent, or Firm* — Harness, Dickey & Pierce, P.L.C.

(57) ABSTRACT

The present invention relates to a pharmaceutical or cosmetic composition and a method for promoting eyelash growth, wherein nipradilol or pharmaceutically or cosmetically acceptable salts thereof are used as active ingredients. The composition of the invention may comprise prostaglandin F2α analogs.

10 Claims, 4 Drawing Sheets

COMPOSITION FOR EYELASH GROWTH

CROSS-REFERENCE TO RELATED APPLICATIONS

This application is a national phase application of PCT Application No. PCT/KR2012/004540, filed on Jun. 8, 2012, which claims the benefit and priority to Korean Patent Application No. 10-2011-005333, filed in the Republic of Korea on May 18, 2011, the entire disclosures of which the applications identified in this paragraph are incorporated herein by references.

FIELD

The present disclosure relates to a composition that helps eyelashes grow or a composition for treatment or prevention of eyelash hypotrichosis. Also, the present disclosure relates to a method of promoting growth of eyelashes.

BACKGROUND

Generally, a healthy individual has about two hundred eyelashes, with women having more than men. Eyelashes grow to be about 1 cm, and vary in direction and angle.

With social and economic development, many people are taking an interest in appearance, with the interest extending towards the appearance of eyelashes. That is, as society is paying more attention to physical appearance, particular focus is put towards accentuating the eyes and extending and volumizing eyelashes and eyebrows for a fuller effect and a good impression. Also, some people simply have sparse hair by nature, or lose eyelashes due to a burn, car accident, disease, infection, continuous makeup, tattoos, stress, and the like. Under these circumstances, an individual experiences great inconvenience as the eyelashes cannot perform its functional feature of protecting the sweat from entering the eye or shielding the eyes from sunlight, dust and the like.

To increase eyelashes, a transplant surgery involving extraction of the hair and hair follicles from the back of the head to the balding spot may be a solution, but this transplant surgery becomes a burden on an individual, both economically and mentally.

Meanwhile, an evaluation index of eyelash increase may include number, thickness, and length of eyelashes, a survey, and the like.

DISCLOSURE

Technical Problem

Accordingly, an object of the present disclosure is to provide a composition that helps eyebrows or eyelashes grow.

Another object of the present disclosure is to provide a method of treating eyebrows or eyelashes that helps the eyebrows or eyelashes grow.

Technical Solution

To achieve the above objects, the present disclosure provides a composition for eyelash growth comprising nipradilol or its pharmaceutically or cosmetically acceptable salts as an active ingredient.

While conducting experiments using various compounds to achieve the above objects, the inventors discovered that nipradilol or its pharmaceutically or cosmetically acceptable salts had the above mentioned effects.

Nipradilol is used to treat glaucoma, however the present study discovered that eyelashes administered with nipradilol were longer, thicker, and fuller than eyelashes not administered with nipradilol. Existing prostaglandin materials such as bimatoprost or latanoprost were already known to increase the number of eyelashes; however the discovery that nipradilol or its pharmaceutically or cosmetically acceptable salts had an even superior effect over bimatoprost was unexpected and surprising. Also, nipradilol or its pharmaceutically or cosmetically acceptable salts according to the present disclosure has an advantage of taking effect earlier in time. Nipradilol is supposed to make richer eyelashes by accelerating the growth period of eyelashes or maintaining its rest period to give the effect of much fuller eyelashes; however, the present disclosure is not limited to this theoretical hypothesis.

In the present disclosure, as the pharmaceutically or cosmetically acceptable salts of nipradilol, salts produced using various inorganic or organic acids may be used. For example, as an appropriate acid, acetate, benzenesulphonate, benzoate, bicarbonate, bitartrate, bromide, calcium edetate, camsylate, carbonate, chloride, bromide, iodide, citrate, dihydrochloride, edetate, edisilate, estolate, esylate, fumarate, gluceptate, gluconate, glutamate, glycollylarsanilate, hexylresorcinate, hydrabamine, hydroxynaphthoate, isethionate, lactate, lactobionate, malate, maleate, mandelate, mesylate, methylsulfate, muscate, napsylate, nitrate, pantothenate, phosphate/diphosphate, polygalacturonate, salycilate, stearate, succinate, sulfate, tannate, tartrate, teoclate, triethiodide, and pamoate (that is, 1,1-methylene-bis-(2-hydroxy-3-naphthoate)) may be used, however the present disclosure is not limited to these specific types. Also, the compound of the present disclosure comprising secondary amine may form the pharmaceutically or cosmetically acceptable salts with various amino acids or the above acids.

In the present disclosure, "eyelash growth" refers to inducing and/or stimulating the growth of eyelashes, and may include reducing the loss of eyelashes.

The composition for eyelash growth according to the present disclosure may additionally comprise one or more of prostaglandin analogues, and the prostaglandin analogues are preferably prostaglandin F2α analogues, and more preferably, the prostaglandin F2α analogues include at least one selected from the group consisting latanoprost, unoprostone, unoprostone isopropyl, bimatoprost, travoprost, tafluprost, carboprost, and pharmaceutically or cosmetically acceptable salts thereof.

For medical aesthetic offerings of eyelashes, the composition of the present disclosure may be in a form of an eye drop, an eye ointment, an eyebrow ointment/lotion, a liquid formulation applicable to a spot where eyelashes grow, a semi-solid formulation directly applicable to a spot where eyelashes grow, and the like, and the eye drop, the eyebrow ointment, and the like may be prepared by a method known to an ordinary person skilled in the art.

Also, the present disclosure provides a method of promoting eyelash grow characterized by treating a therapeutically or cosmetically effective amount of nipradilol or its pharmaceutically or cosmetically acceptable salts to an individual who needs eyelash growth. The treatment may be carried out by an eye drop, an eye ointment, and the like, or may be directly applied to eyelashes using a liquid formulation directly applicable to eyelashes, an eyebrow ointment, an injection, and the like.

Advantageous Effects

The present disclosure provides a pharmaceutical or cosmetic composition that helps eyelashes grow. Also, the present disclosure provides a method of promoting eyelash growth.

DESCRIPTION OF DRAWINGS

In FIGS. 2 through 4, when verifying statistical significance, ** represents $p<0.01$ and * represents $p<0.05$ (t-test, compared to a control group), and n is 8 for each group.

In FIGS. 6 through 8, when verifying statistical significance, ** represents $p<0.01$ and * represents $p<0.05$ (t-test, compared to a control group), # represents $p<0.05$ (t-test, compared to a bimatoprost group), and n is 6 for each group.

MODE FOR DISCLOSURE

Hereinafter, a detailed description is provided through embodiments to help the understanding of the present invention. However, various changes and modifications may be made to the embodiments according to the present disclosure, and it should be understood that the scope of the present disclosure is not intended to be limited to the following embodiments. The embodiments of the present disclosure are provided to give an explanation to an ordinary person skilled in the art more completely.

Embodiment 1

In Vivo Evaluation Related to Eyelash Growth

As a test material, a nipradilol formulation (Hypadil eye drop, 2.5 mg/mL) sold as a medical product and a bimatoprost formulation (Latisse solution, 0.3 mg/mL) was used. In a female mouse, a saline solution, a nipradilol solution or a bimatoprost (positive control group) solution of 2 μl were each applied to the eyelashes by local administration once a day for two weeks. Analysis was conducted immediately after the eyelashes were collected. Using a high-performance microscope with computer-assisted eyelid thickness focus fixation and an image analysis software capable of measuring the number, thickness and length of eyelashes, the eyelashes were measured for the exact number, thickness and length thereof. Numeric data obtained by this method was averaged, and comparative analysis was conducted using prism statistical software.

The result was shown in FIGS. 1 through 4.

Figure 1:
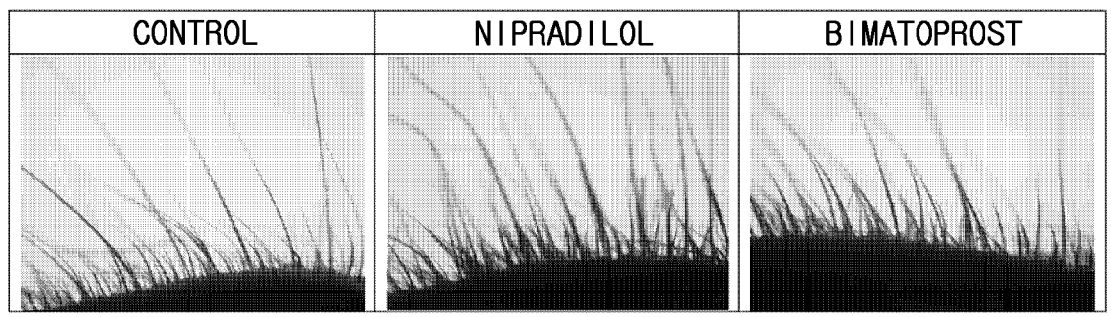
FIG. 1 is a microphotographic image illustrating increases in number, length, and thickness of eyelashes after local administration of nipradilol and the like to the eyelashes for two weeks.

FIG. 1 is a photographic image of the eyelashes of the mouse using a microscope, and shows each representative eyelash image of a control group, a nipradilol treatment group, and a bimatoprost treatment group.

Figure 2:
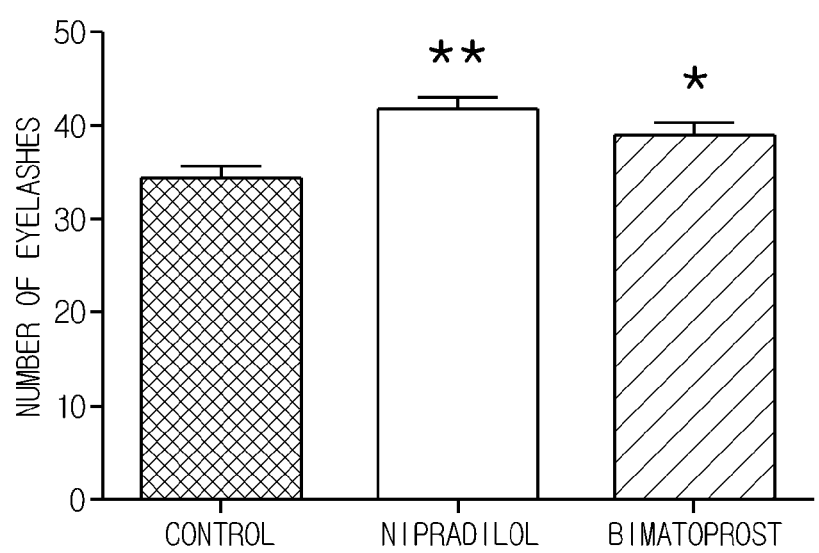
FIG. 2 is a graph illustrating an effect of nipradilol on the number of eyelashes.
Figure 3:
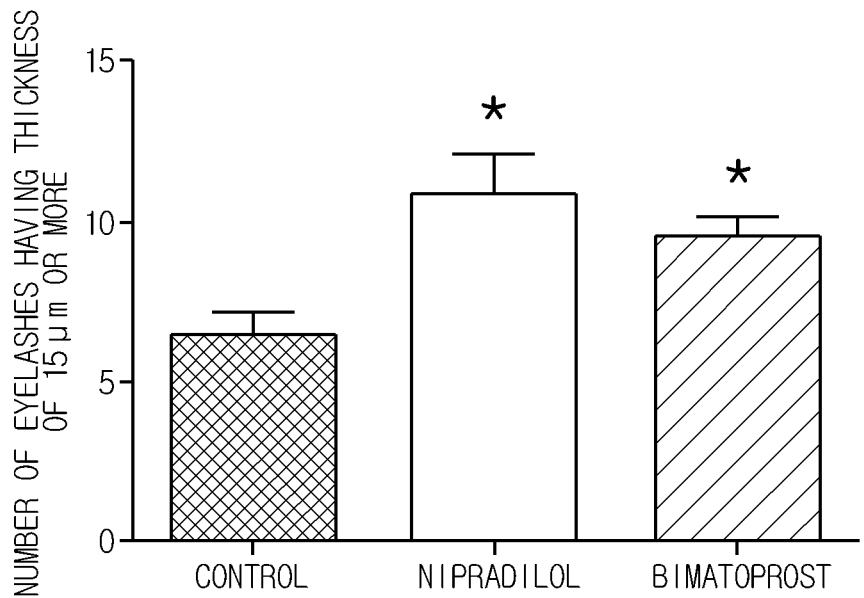
FIG. 3 is a graph illustrating an effect of nipradilol on the thickness of eyelashes.
Figure 4:
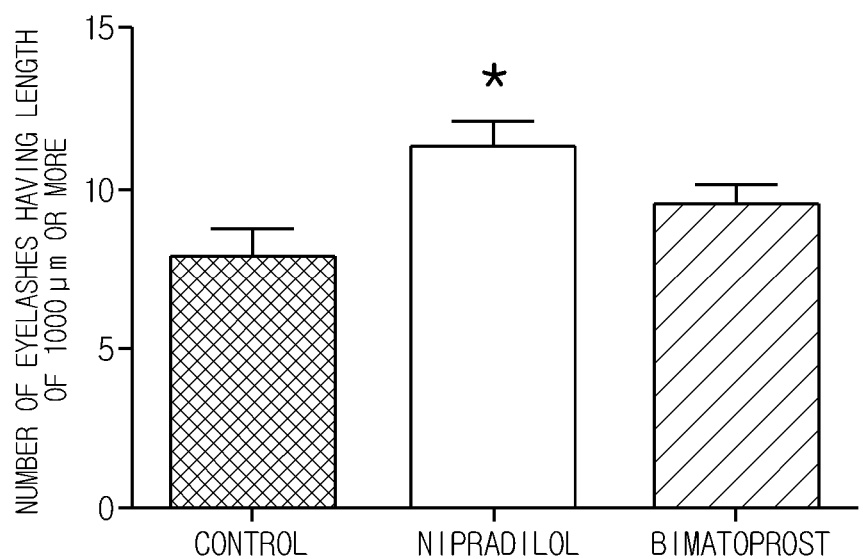
FIG. 4 is a graph illustrating an effect of nipradilol on the length of eyelashes.

As shown in FIGS. 2 through 4, the nipradilol group treated to the eyelashes showing 41.8 eyelashes exhibited an increased effect in the number of eyelashes when compared to the control group showing 34.1 eyelashes and the bimatoprost treatment group showing 39.0 eyelashes. With regard to the number of eyelashes having a thickness of 15 μm or more, the nipradilol group showing 10.9 eyelashes also exhibited an increased effect in the number of eyelashes when compared to the control group showing 6.4 eyelashes and the bimatoprost group showing 9.5 eyelashes. As to the number of eyelashes having a length of 1000 μm or more, the control group showed 7.8 eyelashes, the nipradilol group showed 11.4 eyelashes, and the bimatoprost group showed 9.5 eyelashes, and thus, only the nipradilol group exhibited a statistically significant increasing effect in eyelash length in comparison to the control group.

In conclusion, when nipradilol was administered for two weeks, it was found that these effects showed a statistically significant increase in all the three items of number, thickness, and length of eyelashes, compared to the control group. In contrast, the bimatoprost treatment group showed a statistically significant increase in only two items of number and thickness of eyelashes, compared to the control group.

Embodiment 2

Short-Term In Vivo Evaluation Related to Eyelash Growth

Evaluation was conducted equally to Embodiment 1, but a short-term eyelash change appearing after only one week administration of the test material was measured. The result was shown in FIGS. 5 through 8.

Figure 5:
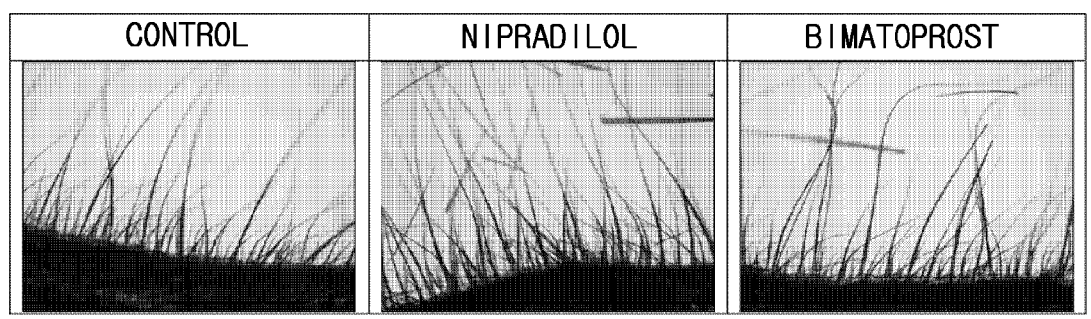
FIG. 5 is a microphotographic image illustrating increases in number, length, and thickness of eyelashes after local administration of nipradilol and the like to the eyelashes for one week.

FIG. 5 is a photographic image of the eyelashes of the mouse using a microscope, and shows each representative eyelash image of a control group, a nipradilol treatment group, and a bimatoprost treatment group.

Figure 6:
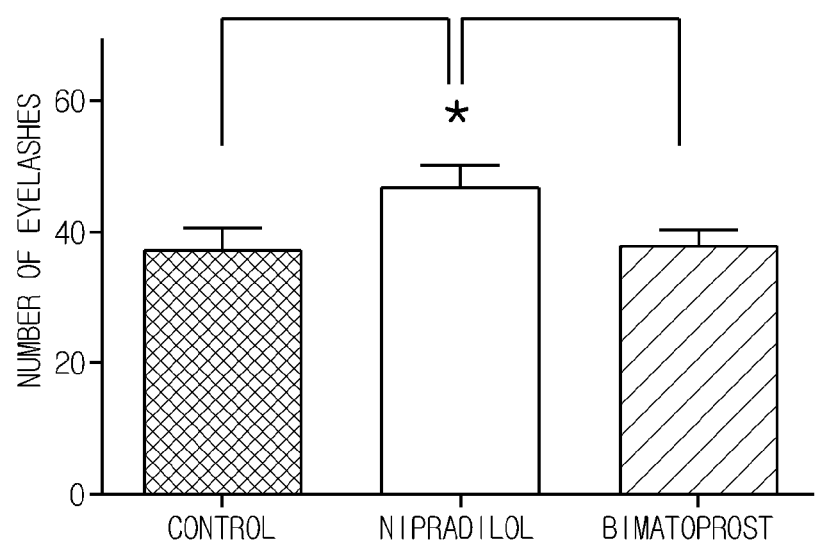
FIG. 6 is a graph illustrating an effect of nipradilol on the number of eyelashes.
Figure 7:
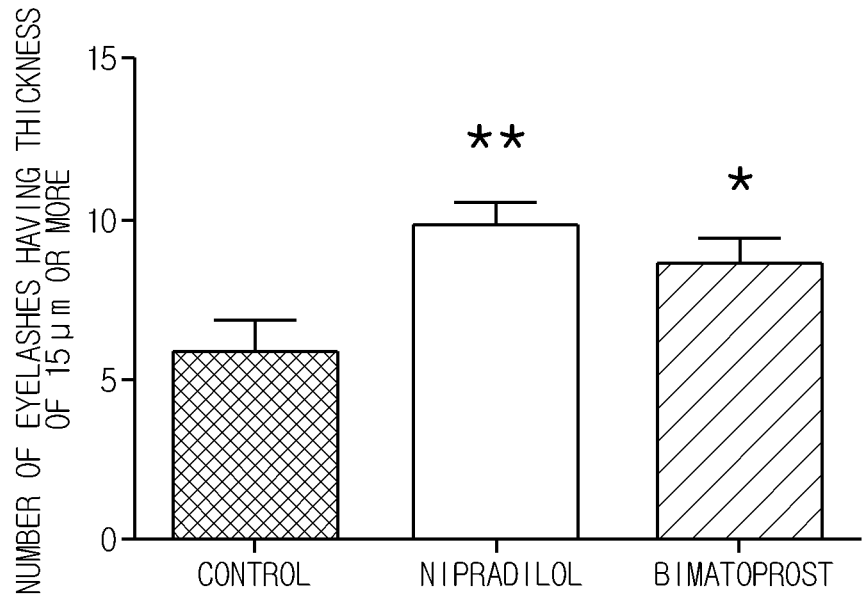
FIG. 7 is a graph illustrating an effect of nipradilol on the thickness of eyelashes.
Figure 8:
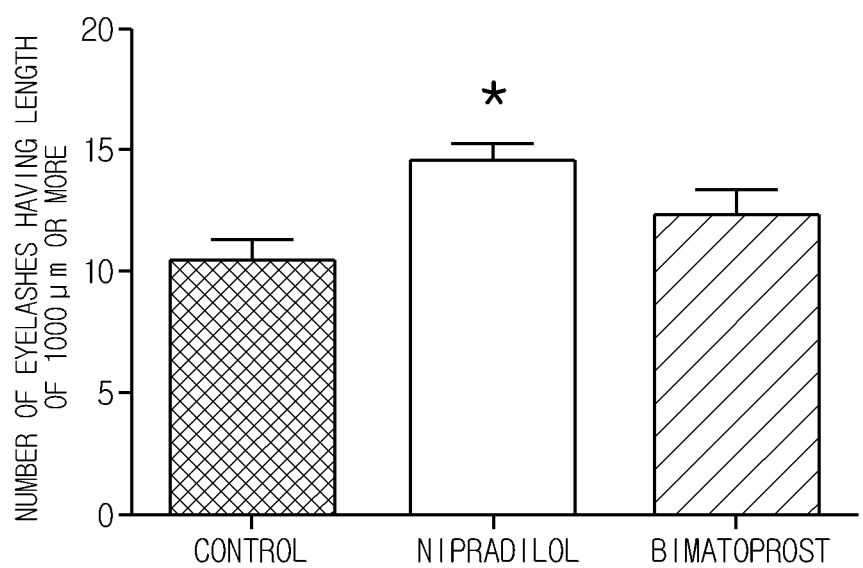
FIG. 8 is a graph illustrating an effect of nipradilol on the length of eyelashes.

As shown in FIGS. 6 through 8, the nipradilol group treated to the eyelashes showing 47.2 eyelashes exhibited an increased effect in the number of eyelashes when compared to the control group showing 36.8 eyelashes. In contrast, the bimatoprost group showed 37.8 eyelashes, and thus, only the nipradilol group had a statistically significant increasing effect in eyelash length, compared to the control group. Also, the eyelash increasing efficacy of the nipradilol group exhibited statistical significance in comparison to the bimatoprost group. With regard to the number of eyelashes having a thickness of 15 μm or more, the control group showed 5.8 eyelashes, the nipradilol administration group showed 9.8 eyelashes, and the bimatoprost administration group showed 8.7 eyelashes. As to the number of eyelashes having a length of 1000 μm or more, the control group showed 10.5 eyelashes, the nipradilol group showed 14.5 eyelashes, and the bimatoprost group showed 12.3 eyelashes, and thus, only the nipradilol group had a statistically significant increasing effect in eyelash length in comparison to the control group.

In conclusion, when evaluating a one week administration, the nipradilol administration group exhibited a statistically significant increase in all the three items of number, thickness, and length of eyelashes, compared to the control group. However, the bimatoprost group exhibited a statistically significant increase in only one item of eyelash thickness. Particularly, nipradilol showed superior efficacy of increasing the number of eyelashes over bimatoprost as a positive control group.

Particularly, when comparing the results of the increase in eyelash number of Embodiment 2, it was found that nipradilol took effect earlier than bimatoprost. That is, a rapid effect was obtained after administration for a relatively short period of time, and accordingly, this is believed to be a great advantage in terms of industrial use.

What is claimed is:

1. A method for eyelash growth comprising:
   administering to a subject in need thereof a composition comprising nipradilol or a pharmaceutically or cosmetically acceptable salt thereof.

2. The method of claim 1, wherein the composition further comprises at least one prostaglandin analogue.

3. The method of claim 2, wherein the prostaglandin analogue is prostaglandin F2α analogue.

4. The method of claim 3, wherein the prostaglandin F2α analogue is selected from the group consisting of latanoprost, unoprostone, unoprostone isopropyl, bimatoprost, travoprost, tafluprost, carboprost and pharmaceutically or cosmetically acceptable salts thereof.

5. The method of claim 1, wherein the composition is a formulation for an external use.

6. The method of claim 5, wherein the formulation is directly applicable to eyelashes.

7. The method of claim 1, wherein the composition is in a form of an eye drop, an eye ointment, an eyebrow ointment, an eyebrow lotion, a liquid formulation or a semi-solid formulation.

8. The method of claim 1, wherein the administration is carried out by applying the composition in the form of an eye drop or an eye ointment to eyelashes of the subject.

9. The method of claim 1, wherein the administration is carried out by injection.

10. The method of claim 1, wherein the composition further comprises at least one prostaglandin analogue selected from the group consisting of latanoprost, unoprostone, unoprostone isopropyl, bimatoprost, travoprost, tafluprost, carboprost and pharmaceutically or cosmetically acceptable salts thereof, and the composition is in a form of an eye drop, an eye ointment, an eyebrow ointment, an eyebrow lotion, a liquid formulation or a semi-solid formulation.

* * * * *